(12) United States Patent
Carolus et al.

(10) Patent No.: US 11,266,380 B2
(45) Date of Patent: Mar. 8, 2022

(54) MEDICAL ULTRASOUND IMAGE PROCESSING DEVICE

(71) Applicant: KONINKLIJKE PHILIPS N.V., Eindhoven (NL)

(72) Inventors: Heike Carolus, Ahrensburg (DE); Julien Senegas, Hamburg (DE); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 609 days.

(21) Appl. No.: 16/306,786

(22) PCT Filed: Jun. 6, 2017

(86) PCT No.: PCT/EP2017/063636
§ 371 (c)(1),
(2) Date: Dec. 3, 2018

(87) PCT Pub. No.: WO2017/211774
PCT Pub. Date: Dec. 14, 2017

(65) Prior Publication Data
US 2019/0142392 A1 May 16, 2019

(30) Foreign Application Priority Data
Jun. 6, 2016 (EP) .................................. 16173091

(51) Int. Cl.
*A61B 8/00* (2006.01)
*A61B 8/08* (2006.01)
(Continued)

(52) U.S. Cl.
CPC .................. *A61B 8/54* (2013.01); *A61B 8/14* (2013.01); *A61B 8/463* (2013.01); *A61B 8/483* (2013.01);
(Continued)

(58) Field of Classification Search
CPC ........... G06T 7/70; G06T 7/0012; G06T 7/10; G06T 7/30; G06T 2207/10136;
(Continued)

(56) References Cited

U.S. PATENT DOCUMENTS 7,925,068 B2 4/2011 Hoctor et al.
9,226,728 B2 1/2016 Hashimoto et al.
(Continued)

FOREIGN PATENT DOCUMENTS

WO 2007148279 A1 12/2007
WO 2009044316 A1 4/2009
(Continued)

OTHER PUBLICATIONS

International Search and Written Opinion for International Application Serial No. PCT/EP2017/063636, dated Sep. 21, 2017, 14 pages.

*Primary Examiner* — Joel Lamprecht

(57) ABSTRACT

The present invention relates to the field of medical ultrasound imaging, and in particular to a medical ultrasound image processing device for supporting reproducible acquisition of 2D ultrasound images. A medical ultrasound image processing device (10) is presented that comprises a first interface (2) for receiving a first 3D scout ultrasound image (3) and a first 2D ultrasound image (4) of a volumetric region; a second interface (5) for receiving a second 3D scout ultrasound image (6) of the volumetric region; and a processing unit (11) arranged to perform the steps of: determining an orientation of an image plane of the first 2D ultrasound image with respect to the first 3D scout ultrasound image (S73); registration of the first 3D scout ultrasound image and the second 3D ultrasound scout image in a common coordinate frame (S75); determining an orientation of the image plane of the first 2D ultrasound image with respect to said common coordinate frame based on said
(Continued)

registration of the first and second 3D scout ultrasound images and the determined orientation of the image plane of the first 2D ultrasound image with respect to the first 3D scout ultrasound image (S76); and providing a control signal adapted to control an acquisition of a second 2D ultrasound image of the volumetric region by an ultrasound probe in accordance with the orientation of the image plane of the first 2D ultrasound image of the volumetric region (S77), wherein an orientation of an image plane of the second 2D ultrasound image corresponds to the determined orientation of the image plane of the first 2D ultrasound image of the volumetric region, wherein the acquisition of the second 2D ultrasound image by the ultrasound probe is from either a same position as, or a tracked position with respect to, the position of the acquisition of the second 3D scout ultrasound image.

22 Claims, 5 Drawing Sheets

(51) Int. Cl.
| | |
|---|---|
| *G06T 7/30* | (2017.01) |
| *G06T 7/70* | (2017.01) |
| *G06T 7/00* | (2017.01) |
| *A61B 8/14* | (2006.01) |
| *G06T 7/10* | (2017.01) |

(52) U.S. Cl.
CPC .......... *A61B 8/5246* (2013.01); *A61B 8/5253* (2013.01); *G06T 7/0012* (2013.01); *G06T 7/10* (2017.01); *G06T 7/30* (2017.01); *G06T 7/70* (2017.01); *A61B 8/0866* (2013.01); *A61B 8/0883* (2013.01); *A61B 8/4245* (2013.01); *G06T 2207/10136* (2013.01); *G06T 2207/30004* (2013.01)

(58) Field of Classification Search
CPC ............ G06T 2207/30004; A61B 8/54; A61B 8/5246; A61B 8/14; A61B 8/463; A61B 8/5253; A61B 8/483; A61B 8/4245; A61B 8/0866; A61B 8/0883
See application file for complete search history.

(56) References Cited

U.S. PATENT DOCUMENTS

| | | |
|---|---|---|
| 2006/0020204 A1 | 1/2006 | Serra et al. |
| 2008/0187193 A1 | 8/2008 | Hoctor et al. |
| 2008/0262348 A1 | 10/2008 | Hashimoto et al. |
| 2010/0268085 A1 | 10/2010 | Kruecker et al. |
| 2016/0007970 A1 | 1/2016 | Dufour et al. |
| 2016/0045186 A1 | 2/2016 | Cong et al. |
| 2018/0153504 A1* | 6/2018 | Herickhoff ............. A61B 8/085 |

FOREIGN PATENT DOCUMENTS

| | | |
|---|---|---|
| WO | 2013134559 A1 | 9/2013 |
| WO | 2015092628 A1 | 6/2015 |
| WO | 2015170304 A1 | 12/2015 |

* cited by examiner

MEDICAL ULTRASOUND IMAGE PROCESSING DEVICE

This application is the U.S. National Phase application under 35 U.S.C. § 371 of International Application No. PCT/EP2017/063636, filed on Jun. 6, 2017, which claims the benefit of European Application Serial No. 16173091.6, filed Jun. 6, 2016. These applications are hereby incorporated by reference herein.

FIELD OF THE INVENTION

The present invention relates to the field of medical ultrasound imaging. In particular, the present invention relates to a medical ultrasound image processing device for supporting reproducible acquisition of 2D ultrasound images. The present invention further relates to a corresponding method and ultrasound system. Still further, the present invention relates to a computer program comprising program code means for causing a computer to carry out the steps of said method.

BACKGROUND OF THE INVENTION

Medical ultrasound imaging is typically a dynamic examination wherein an ultrasound probe is manually moved over a region of interest by a physician. Hence, in contrast to imaging modalities such as CT or MRI, wherein a subject is positioned with a known orientation relative to the imaging system, an ultrasound examination strongly depends on the physician carrying out the examination. For example, one and the same structure, such as an organ or tumor, may be classified to have different sizes based on images taken by different physicians. In clinical practice, such measurements are typically performed based on 2D ultrasound images.

US 2006/0020204 A1 discloses a system and method for three-dimensional space management and visualization of ultrasound data. Instead of visualizing ultrasound images just as 2D images, it is suggested to visualize already acquired ultrasound images as positionally and orientally located slices within a particular 3D space.

SUMMARY OF THE INVENTION

It is an object of the present invention to provide a device and method which support more consistent and/or reliable acquisition of 2D ultrasound images.

In a first aspect of the present invention a medical ultrasound image processing device is presented that comprises:

a first interface for receiving a first 3D scout ultrasound image and a first 2D ultrasound image of a volumetric region;

a second interface for receiving a second 3D scout ultrasound image of the volumetric region; and a processing unit arranged to perform the steps of:
determining an orientation of an image plane of the first 2D ultrasound image with respect to the first 3D scout ultrasound image;
registration of the first 3D scout ultrasound image and the second 3D scout ultrasound image in a common coordinate frame;
determining an orientation of the image plane of the first 2D ultrasound image with respect to said common coordinate frame based on said registration of the first and second 3D scout ultrasound images and the determined orientation of the image plane of the first 2D ultrasound image with respect to the first 3D scout ultrasound image; and
providing a control signal adapted to control an acquisition of a second 2D ultrasound image of the volumetric region by an ultrasound probe in accordance with the orientation of the image plane of the first 2D ultrasound image of the volumetric region,
wherein an orientation of an image plane of the second 2D ultrasound image corresponds to the determined orientation of the image plane of the first 2D ultrasound image of the volumetric region,
wherein the acquisition of the second 2D ultrasound image by the ultrasound probe is from either a same position as, or a tracked position with respect to, the position of the acquisition of the second 3D scout ultrasound image.

In a second aspect of the present invention a medical image processing method is presented, the method comprising the steps of:

obtaining (i.e., receiving or retrieving) a first 3D scout ultrasound image and a first 2D ultrasound image of a volumetric region;

obtaining (i.e., receiving or retrieving) a second 3D scout ultrasound image of the volumetric region;

determining an orientation of an image plane of the first 2D ultrasound image with respect to the first 3D scout ultrasound image;

registration of the first 3D scout ultrasound image and the second 3D scout ultrasound image in a common coordinate frame;

determining an orientation of the image plane of the first 2D ultrasound image with respect to said common coordinate frame based on said registration of the first and second 3D scout ultrasound images and the determined orientation of the image plane of the first 2D ultrasound image with respect to the first 3D scout image; and providing a control signal adapted to control an acquisition of a second 2D ultrasound image of the volumetric region by an ultrasound probe in accordance with the orientation of the image plane of the first 2D ultrasound image of the volumetric region, wherein an orientation of an image plane of the second 2D ultrasound image corresponds to the determined orientation of the image plane of the first 2D ultrasound image of the volumetric region, wherein the acquisition of the second 2D ultrasound image by the ultrasound probe is from either a same position as, or a tracked position with respect to, the position of the acquisition of the second 3D scout ultrasound image.

In a further aspect of the present invention an ultrasound system for imaging a volumetric region is presented, the system comprising:

an ultrasound probe comprising an ultrasound transducer array arranged to acquire an ultrasound image of a subject;

the aforementioned medical ultrasound image processing device; and a probe controller arranged to control the ultrasound probe to acquire the second 2D ultrasound image based on the control signal provided by said medical ultrasound image processing device from either a same position as, or at a tracked position with respect to, the position of the acquisition of the second 3D scout ultrasound image.

In yet further aspects of the present invention, there are provided a corresponding computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium can have similar and/or identical preferred embodiments as the claimed device, in particular as defined in the dependent claims and as disclosed herein.

The present invention is based on the idea of using 3D scout ultrasound images for establishing a correspondence between a first and a second 2D ultrasound image. The solution presented herein is particularly advantageous for providing comparable 2D ultrasound images from a first, initial 2D ultrasound examination and a second, follow-up 2D ultrasound examination.

The first and the second 3D scout ultrasound images can be registered to determine their relative position and orientation. Hence, based on a relative position and orientation of the first 2D ultrasound image with respect to the first 3D scout ultrasound image, and further based the relative position and orientation of the first 3D scout ultrasound image with respect to the second 3D scout ultrasound image, a relative position and orientation for acquisition of the second 2D ultrasound image with respect to the second 3D scout ultrasound image can be calculated, such that the position and orientation of said second 2D ultrasound image corresponds to the position and orientation of the first 2D ultrasound image with respect to the examined volumetric region. In other words, a second, follow-up 2D ultrasound image with the same view as the initial 2D ultrasound image can be acquired.

In conventional 2D ultrasound systems, the acquisition of consistent and reproducible 2D ultrasound images is challenging and strongly depends on how the physician carrying out the examination positions the handheld ultrasound probe. Yet, if the view of follow-up examinations is not the same, also measurements may not be identical and comparisons between them are not reliable. In current clinical practice, small deviations between an initial and a follow-up ultrasound images are therefore often attributed to measuring inaccuracy. There is thus a need to enable more accurate measurements. For example, early detection of even small size changes of a lesion may change a therapy regime for the benefit of the patient.

To bypass this challenge it is proposed herein to employ a first and a second 3D scout ultrasound scan for alignment of a first 2D ultrasound image and a second 2D ultrasound image to be acquired. 3D ultrasound is feasible since it does not harm the patient and is acquired quickly, for example in $1/10^{th}$ of a second. The first 3D scout ultrasound image and the first 2D ultrasound image can be stored together with information or data indicative of their relative position and/or orientation. This data can be received by the image processing device together with the first 3D scout ultrasound image and the first 2D ultrasound image. For example, the coordinates and orientation of the first 2D ultrasound image with respect to the first 3D scout ultrasound image can be stored. Alternatively or in addition, control parameters for acquisition of the first 2D ultrasound image and the first 3D scout ultrasound image with a 3D ultrasound probe may be stored. When a second, follow-up 2D ultrasound image with an identical view is required, a second 3D scout ultrasound scan be acquired and registered with the first, initial 3D scout ultrasound image. Through the knowledge of their correspondence and the relative orientation and/or position of the first, initial 2D ultrasound image with respect to the first 3D scout ultrasound image, the corresponding control signal for acquisition of the second, follow-up 2D ultrasound image can be deduced and the follow-up 2D ultrasound image with an identical view as the initial 2D ultrasound image can be acquired.

The proposed solution can thus support more consistent and/or reliable acquisition of 2D ultrasound images with an ultrasound system. By providing a control signal for acquisition of the second 2D ultrasound image in accordance with the orientation of the image plane of the first 2D ultrasound image of the volumetric region, the proposed medical image processing apparatus can thus enable the acquisition of 2D slices in a follow-up examination in accordance with the 2D slices in the previous examination.

As a further advantage, the time required by a physician for acquisition of a consistent follow-up ultrasound image may be reduced. Hence, instead of acquisition of an entire high resolution 3D ultrasound scan, it can be sufficient to acquire a 3D scout ultrasound image having a reduced resolution and then acquiring the specific follow-up 2D ultrasound image of interest which corresponds the initial, first 2D ultrasound image.

It should further be noted that in particular for time critical examinations such as an examination of a beating heart, a high resolution 3D scan may not be fast enough. In this case additional techniques such as gated acquisition would be required. A further advantage of the solution proposed herein can thus be a reduced complexity.

As a further advantage, a less trained physician may be supported in acquisition of comparable follow-up 2D ultrasound images. For example, the first 2D ultrasound image and the first 3D scout ultrasound image may have been acquired by a highly qualified specialist, whereas the follow-up ultrasound images may be acquired by an assistant.

Generally speaking, a first (scout) ultrasound image can refer to an initial examination and a second (scout) ultrasound image can refer to a follow-up examination. A follow-up examination may be carried out at a later point in time, for example a few weeks or months after the initial examination, to assess a healing process or progression of a disease. For example, the first 3D scout ultrasound image and the first 2D ultrasound image are acquired together at the initial examination, whereas the second 3D scout ultrasound image and the second 2D ultrasound image are subsequently acquired at the follow-up examination.

The first ultrasound images and the second ultrasound images can be images acquired with the same or a different ultrasound system. For example, the initial ultrasound images can be acquired at a hospital, whereas the second, follow-up ultrasound images are acquired in private practice. The first ultrasound images may be obtained, for example, from a database such as an electronic health record (EHR).

It shall be understood that the first interface and the second interface can be the same interface such as one single hardware interface or can also be different interfaces. For example, the first interface and the second interface can be one common data interface, i.e. an interface for receiving the first 3D scout ultrasound image, the first 2D ultrasound image and the second 3D scout ultrasound image of the volumetric region. In an embodiment, the first interface can be, for example, a data network interface for receiving the first 3D scout ultrasound image and the first 2D ultrasound image, whereas the second interface may be an interface for receiving data directly from an ultrasound acquisition unit. The first interface can be seen in a functional way as indicating data from an initial examination, whereas the second interface indicates data from a follow-up examination.

3D ultrasound images may be acquired by a mechanically steered array or electronically. Electronical steering can be enabled by a 2D ultrasound transducer array. Alternatively, mechanical steering of 1D ultrasound transducer array may be used to acquire a 3D ultrasound image.

A 3D scout ultrasound image as used herein refers to a 3D ultrasound image, in particular a 3D ultrasound image having a lower resolution than a 2D ultrasound image. Advantageously, lower resolution first and/or second 3D ultrasound images can be used to provide a fast acquisition time. This is particularly advantageous when imaging a moving organ such as the heart. The first and/or second 2D ultrasound images may be acquired with a higher resolution.

Image registration is a common term in medical imaging for determining a relative position and/or orientation of two 2D or 3D images relative to each other. Reference can be made to WO 2002/16963 A2 and the additional disclosures cited therein. For example, corresponding regions of images can be identified by edge detection and segmentation algorithms.

A common coordinate frame can refer to a coordinate frame of the first or second 3D scout ultrasound image or an arbitrarily oriented coordinate frame, in general any coordinate system which may serve as a reference. The relative orientation of the ultrasound images with respect to each other matters.

In an embodiment, the first 3D scout ultrasound image and the first 2D ultrasound image can be images acquired with a first 3D ultrasound probe from a first position. The second 3D scout ultrasound image can be an image acquired with a second 3D ultrasound probe from a second position, for example after repositioning the ultrasound probe or in a follow-up examination. The first 3D ultrasound probe and the second 3D ultrasound probe may thus refer to the same or different ultrasound probes. After acquisition of the second 3D scout ultrasound image, the control signal can then be provided for acquisition of the second 2D ultrasound image based on said control signal from said second position. Advantageously, the ultrasound probe is not moved substantially between the respective 3D scout ultrasound image and the corresponding 2D ultrasound image. Thereby, the first 3D scout ultrasound image and the first 2D ultrasound image are images acquired from the same, first position. Correspondingly, the second 3D scout ultrasound image and the second 2D ultrasound image will advantageously both be acquired from the second position. An advantage of this embodiment is that a position and/or orientation of the first 2D ultrasound image with respect to the first 3D scout ultrasound image can be determined based on system parameters of the ultrasound system for acquisition of said ultrasound images, such as for example beam steering parameters. It is thus not necessary to track a position of the ultrasound probe—even though this would also be possible in the alternative or in addition. Advantageously, for example when having a 3D ultrasound system with a matrix transducer, the position and/or orientation of the image plane for acquisition of the second 2D ultrasound image can be set electronically, i.e., via electronic beam steering. It is to be understood that the processing unit can be arranged accordingly. Generally speaking, the respective 2D and 3D ultrasound image have to be stored and will be received together with data indicative of their relative position and/or orientation with respect to each other.

In a refinement, for example, if the ultrasound probe was slightly moved between acquisition of the 3D scout ultrasound image and the 2D ultrasound image, the position and/or orientation of the 2D ultrasound image relative to the 3D scout ultrasound image may still be determined, e.g., by means of registration. Furthermore, such information can be stored for any subsequently acquired 2D ultrasound image in the vicinity. By this means, one 3D scout ultrasound image can serve as a basis for several 2D ultrasound images.

In an embodiment, the processing unit can be arranged to determine the orientation of the image plane of the first 2D ultrasound image with respect to the first 3D scout ultrasound image based on control parameters of the ultrasound probe for acquisition of the first 2D ultrasound image and the first 3D scout ultrasound image. Control parameters for acquisition of the respective 2D and 3D ultrasound images can be indicative of an orientation and/or position of said ultrasound images with respect the ultrasound probe. Provided that the ultrasound images are acquired from the same position, i.e. the ultrasound probe has not moved substantially, the relative position and/or orientation of the 2D ultrasound image and the 3D scout ultrasound image can thus be derived from the control parameters of the ultrasound probe. In particular, such control parameters may comprise beam steering parameters, in particular for electronic beam steering. Correspondingly, the control signal of the processing unit can provide one or more control parameters for acquisition of second 2D ultrasound image, such as beam steering parameters for acquisition of the second 2D ultrasound image at a desired orientation and/or position with respect to the second 3D scout ultrasound image and in correspondence with an orientation and/or position of the first 2D ultrasound image. Alternatively or in addition, the orientation and/or position of the image plane of the first 2D ultrasound image with respect to the first 3D scout ultrasound image can also be determined based on 2D to 3D registration. This is particularly helpful if the control parameter information is not available or insufficient. These techniques can also be combined to further improve the performance.

In an embodiment, at least one of the ultrasound images further can comprise metadata indicative of a control parameter of an ultrasound probe for acquisition of said ultrasound image, in particular indicative of at least one of an acquisition gain, focus, depth, zoom, position, orientation and beam steering parameter. An advantage of this embodiment is that said one or more control parameters can directly be stored together with the ultrasound image data. Alternatively or in addition, the medical image processing device may receive data regarding one or more control parameters (also referred to as system parameters) separately via an interface.

In an embodiment, the control signal provided by the processing unit can be indicative of at least one control parameter of the ultrasound probe for acquisition of the second 2D ultrasound image. For example, the control signal can be indicative of at least one of an acquisition gain, focus, depth, zoom, position, orientation and a beam steering parameter. Thereby, the ultrasound probe can be controlled to acquire a second 2D ultrasound image which provides a corresponding view as the first 2D ultrasound image. Alternatively, the control signal may also provide a control signal indicative of a relative position and/or orientation of the desired second 2D ultrasound image to be acquired with respect to the second 3D scout ultrasound image. The control parameters for the ultrasound probe, in particular for beam steering, can be calculated based thereon by an optional intermediate entity such as a probe or transducer controller.

In an embodiment, the step of registration can comprise an anatomy segmentation in said first and second 3D scout ultrasound images. A definition of said common coordinate frame can be based on said anatomy segmentation. An advantage of this embodiment is that anatomic features can be taken as a reference for determining the relative position and orientation of the first and second 3D scout ultrasound images.

In an embodiment, the registration of the second 3D scout ultrasound image with the first 3D scout ultrasound image can comprise a registration of an image content within field-of-view masks of said first 3D ultrasound image and said second 3D ultrasound image respectively. An advantage of this embodiment is, that not the entire ultrasound image is considered for the registration but only an image content within a relevant area as indicated by a field-of-view mask. Hence, the image content and not the field-of-view cones as such can be compared and registered. A field view cone can be the typical triangular or pyramidal view cone provided by an ultrasound probe.

In an embodiment, the registration can comprise determining an overlap between the first 3D scout ultrasound image and the second 3D scout ultrasound image, in particular determining whether there is a sufficient overlap of said 3D ultrasound images. Thereby, a sufficient overlap for registration of said 3D ultrasound images can be determined. A further advantage is that an alert signal can be generated by the image processing device if an insufficient overlap is determined. In consequence, an alert message can be provided via a user interface, for example via a separate or an already existing user interface of the ultrasound system, and the user may reposition the ultrasound probe accordingly. Advantageously, the user can be provided with guidance on how to position the ultrasound probe based on the determined overlap. For example, the user may be instructed to move or tilt the ultrasound probe in a certain direction. Such guidance can be provided, for example, by voice guidance with real-time feedback on how to position the probe and/or via a graphical user interface. The graphical user interface can advantageously show a current and a target position of the ultrasound probe and/or which probe displacements are required.

In a refinement, a sequence of 3D scout ultrasound images can be iteratively acquired until a sufficient overlap has been found. The image processing device can thus be arranged to provide a control signal for iterative acquisition of 3D scout ultrasound images. If a sufficient overlap has been detected, the user can be notified accordingly via a user interface.

In an embodiment, a resolution of the first and/or second 2D ultrasound image can be higher than a resolution of the first and/or second 3D scout ultrasound image. For example, the ultrasound system may be arranged to acquire the 2D ultrasound image with a higher resolution than the corresponding 3D scout ultrasound image. It has been found that a lower resolution 3D scout ultrasound image can be sufficient for registration. A higher resolution 2D ultrasound image may then be used for actual clinical diagnostics. An advantage of this embodiment is that in particular the first 3D scout ultrasound image may be quickly acquired in addition to the first 2D ultrasound image. For example, the acquisition of the 3D scout ultrasound image may only take $1/10^{th}$ of a second. Hence, during a time when an operator of the ultrasound system freezes the screen for detailed analysis of a 2D ultrasound image, a background process for acquisition of a 3D scout ultrasound image having a reduced resolution may be performed, essentially without loss of time.

In an embodiment, the processing unit can be further arranged to determine a position of the first 2D ultrasound image with respect to the first 3D scout ultrasound image and/or the common coordinate frame and further arranged to provide a control signal adapted to control an acquisition of the second 2D ultrasound image by an ultrasound probe in accordance with the position of the first 2D ultrasound image of the volumetric region. It should be understood that a position and orientation of the second 2D ultrasound image may correspond to the position and orientation of the first 2D ultrasound image. Hence, the processing unit can be arranged to consider both the position and the orientation in each respective step. Advantageously, same structures are thus shown at the same position in the first and the second 2D ultrasound images.

In an embodiment, the medical image processing device, in particular the processing unit, can be arranged to provide guidance to a sonographer for acquisition of the second 2D ultrasound image based on said control signal via a user interface. In particular voice guidance or graphical guidance on how to position the ultrasound probe can be provided via the user interface to the sonographer based on the control signal for acquisition of the second 2D ultrasound image in accordance with the first 2D ultrasound image. For example, the sonographer can be provided with feedback via a human-machine-interface (HMI) on how to position the ultrasound probe for acquisition of the second 2D ultrasound image in correspondence with the first 2D ultrasound image. For example, guidance can be provided sonographer for the acquisition of the follow-up 2D ultrasound image by voice guidance, advantageously with real-time feedback, on how to position the probe and/or on a graphical display. Such guidance can advantageously indicate a current and a target position of the ultrasound probe and/or which probe displacements are required. For example, registration information indicative of the registration of the first 3D scout ultrasound image and the second 3D scout ultrasound image, such as position and/or orientation of the 3D scout ultrasound images with respect to each other, can be provided on a graphical user interface as a help for the sonographer to move the ultrasound probe in a way that the probe position and/or orientation corresponds better between the first and the second acquisition.

In an embodiment, the aforementioned method can further comprise the step of acquisition of the second 2D ultrasound image of the volumetric region with the ultrasound probe based on said control signal. Correspondingly, the method can further comprise the preceding steps of acquisition of the first 2D ultrasound image and the first 3D scout ultrasound image, for example in an initial first examination, as well as the step of acquiring the second 3D scout ultrasound image, for example immediately before acquisition of the second 2D ultrasound image based on said control signal, in a follow-up examination.

It is to be understood, that the acquired ultrasound images or more precisely the ultrasound image data can be obtained and processed by a processing unit. As used herein the term obtaining can refer to receiving or retrieving data. For example, ultrasound image data which has previously been acquired with an ultrasound probe is received by the medical ultrasound image processing device. It is also possible to actively retrieve such data from a storage unit or database such as an electronic health record (EHR), hospital information system (HIS) or picture archiving and communication system (PACS). Advantageously, the first 2D ultrasound image and the first 3D scout ultrasound image are stored in a database together with data indicative of their relative position and/or orientation. When performing a follow-up examination, this information can be accessed, received and used for determining the control signal for consistent and reliable acquisition of the second 2D ultrasound image.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Before referring to the medical ultrasound image processing device 10 according to an aspect of the present invention, the basic principles of an ultrasound system 100 shall be explained with reference to FIGS. 1 and 2.

Figure 1:
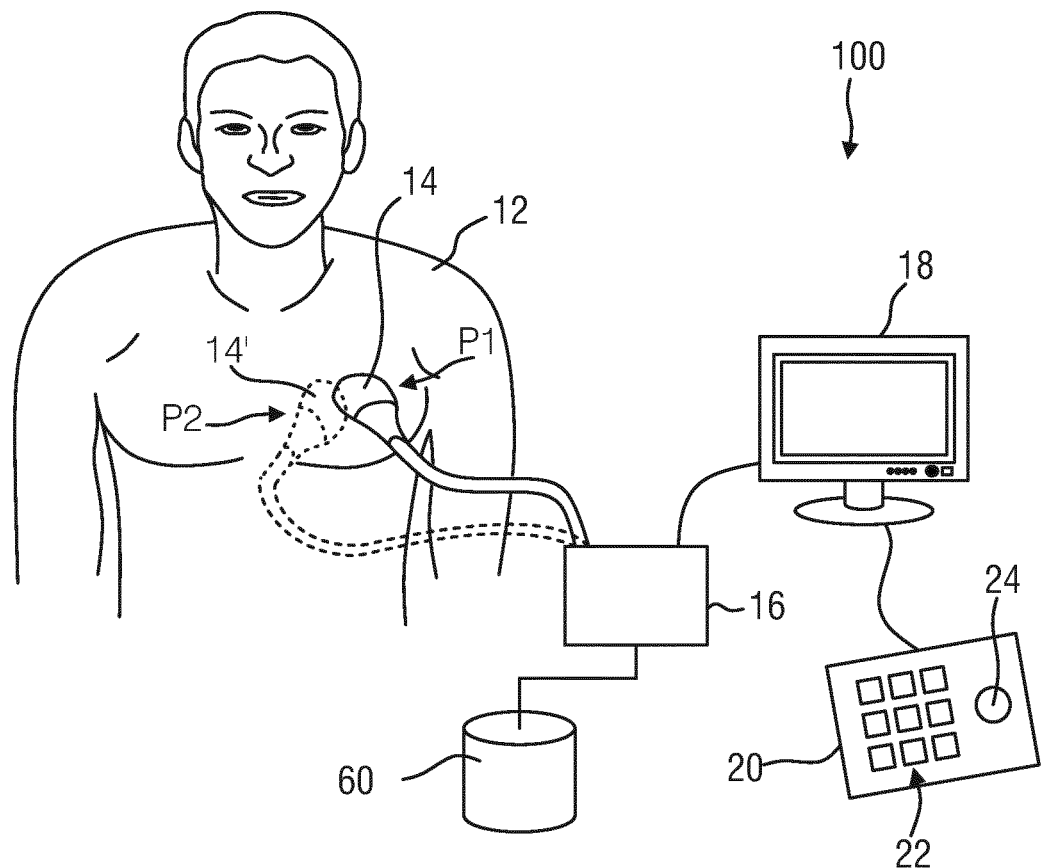
FIG. 1 shows a schematic representation of an ultrasound imaging system in use to scan a part of a patient's body.

FIG. 1 shows a schematic illustration of an ultrasound system 100, in particular a medical three-dimensional (3D) ultrasound imaging system. The ultrasound imaging system 100 is applied to inspect a volume of an anatomical site, in particular an anatomical site of a patient 12 over time. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements are preferably arranged in a two-dimensional array, in particular for providing a multi-planar or three-dimensional image.

A particular example for a three-dimensional ultrasound system which may be the CX40 Compact Xtreme ultrasound system sold by the applicant, in particular together with an X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied in conjunction with the current invention.

A 3D ultrasound scan typically involves emitting ultrasound waves that illuminate a particular volume within a body, which may be designated as target volume or volumetric region. This can be achieved by emitting ultrasound waves at multiple different angles. A set of volume data is then obtained by receiving and processing reflected waves. The set of volume data is a representation of the target volume within the body over time. Since time is usually denoted as fourth dimension, such ultrasound system 100 delivering a 3D image sequence over time, is sometimes also referred to a 4D ultrasound imaging system.

It shall be understood that the ultrasound probe 14 may either be used in a non-invasive manner (as shown in FIG. 1) or in an invasive manner as this is usually done in TEE (not explicitly shown). The ultrasound probe 14 may be hand-held by the user of the system, for example medical staff or a physician. The ultrasound probe 14 is applied to the body of the patient 12 so that an image of an anatomical site, in particular an anatomical object of the patient 12 is provided.

Further, the ultrasound system 100 may comprise an image reconstruction unit 16 that controls the provision of a 3D image sequence via the ultrasound system 100. As will be explained in further detail below, the image reconstruction unit 16 may control not only the acquisition of data via the transducer array of the ultrasound probe 14, but also signal and image processing that form the 3D image sequence out of the echoes of the ultrasound beams received by the transducer array of the ultrasound probe 14.

The ultrasound system 100 may further comprise a display 18 for displaying the 3D image sequence to the user. Still further, an input device 20 may be provided that may comprise keys or a keyboard 22 and further inputting devices, for example a trackball 24. The input device 20 might be connected to the display 18 or directly to the image reconstruction unit 16.

Figure 2:
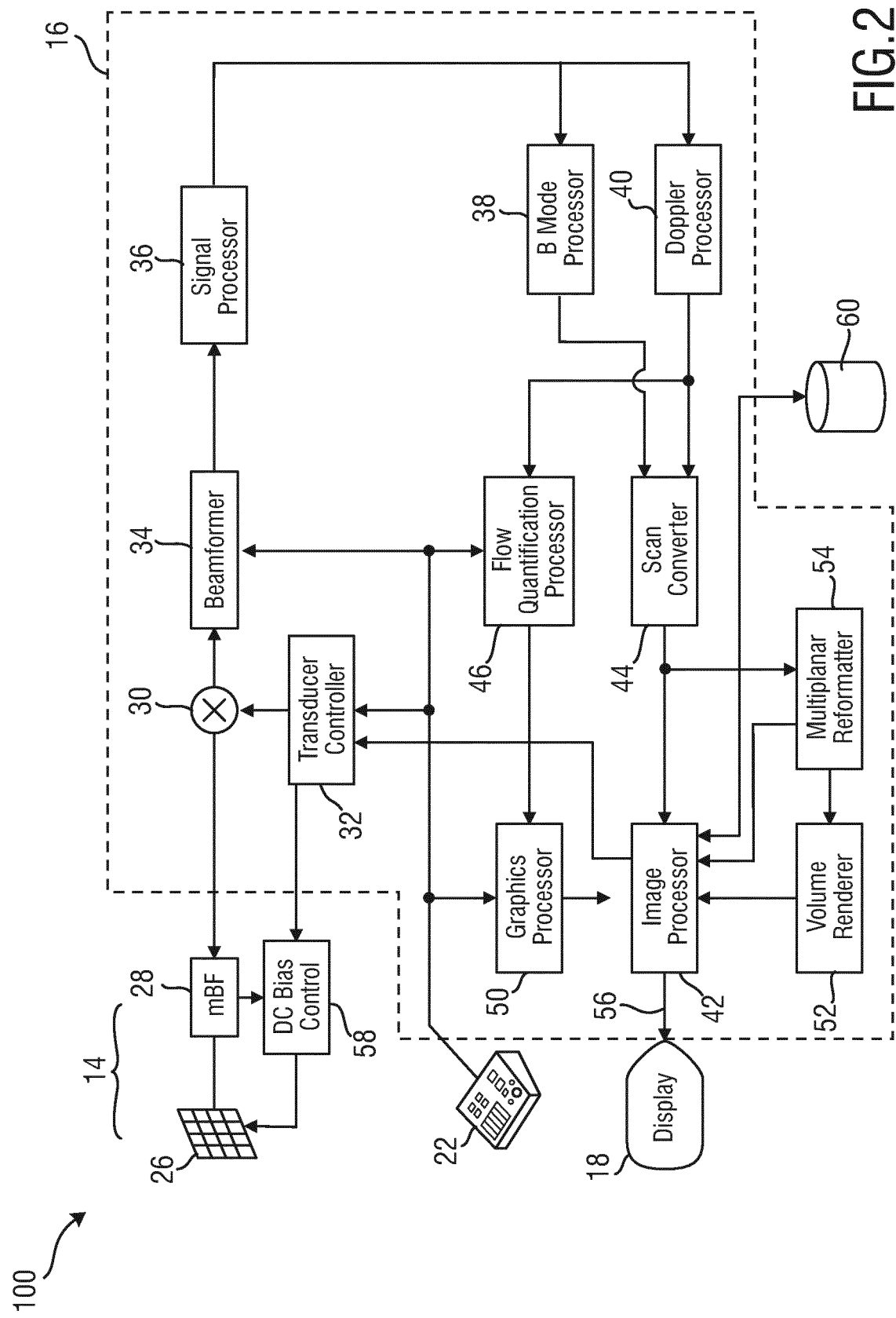
FIG. 2 shows a schematic block diagram of an embodiment of an ultrasound imaging system with an array transducer.

FIG. 2 illustrates a schematic block diagram of the ultrasound system 100. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field. The multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18. In addition to being used for imaging, the blood flow values produced by the Doppler processor 40 and tissue structure information produced by the B mode processor 38 may be transferred to a quantification processor 46. This quantification processor 46 may produce measures of different flow conditions such as the volume rate of blood flow as well as structural measurements such as the sizes of organs and gestational age. The quantification processor 46 may receive input from the user control panel 22, such as the point in the anatomy of an image where a measurement is to be made. Output data from the quantification processor 46 may be transferred to a graphics processor 50 for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images.

Again, it shall be noted that the aforementioned ultrasound system 100 has only been explained as one possible example for an application of the medical ultrasound image processing device 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components do not necessarily have to be realized as hardware, but may also be realized as software components. A plurality of the aforementioned components may also be comprised in common entities or even in one single entity and do not all have to be realized as separate entities, as this is schematically shown in FIG. 2.

Figure 3:
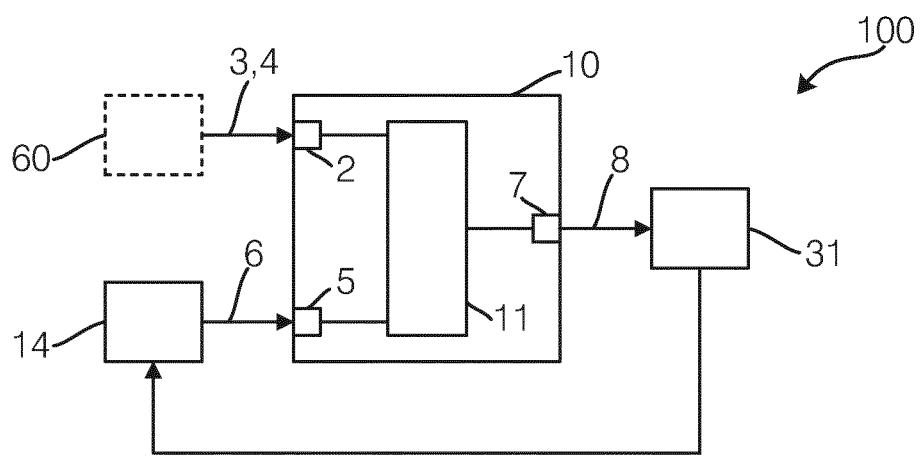
FIG. 3 shows a simplified schematic block diagram of an ultrasound system comprising a medical image processing device according to an aspect of the present invention.

FIG. 3 shows a simplified schematic block diagram of an ultrasound system 100 comprising a medical ultrasound image processing device 10 according to an aspect of the present invention. The image processing device 10 receives a first 3D scout ultrasound image 3 and a first 2D ultrasound image 4 of a volumetric region, for example from an initial examination, as well as a second 3D scout ultrasound image 6 of the volumetric region, for example from a current follow-up examination, as inputs. As an output, the image processing device 10 provides a control signal 8 adapted to control an acquisition of a second 2D ultrasound image of the volumetric region by an ultrasound probe 14 in accordance with the orientation of the image plane of the first 2D ultrasound image 4 of the volumetric region.

Figure 5:
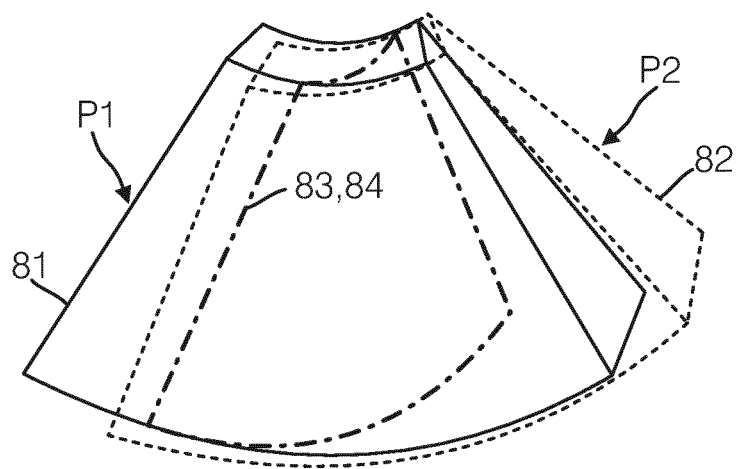
FIG. 5 shows a first schematic illustration of an orientation of respective 2D and 3D ultrasound images with respect to each other.

Due to the handheld acquisition of ultrasound images, wherein the ultrasound probe 14 is manually positioned by the physician, a position P1 of the ultrasound probe 14 during the initial examination will normally differ from a position P2 of the ultrasound probe 14' during the follow-up examination of the volumetric region. This is exemplarily shown in FIG. 1. Hence, as shown in FIG. 5, a pyramidal view cone 81 of the first 3D scout ultrasound scan from the first position P1 can differ from a pyramidal view cone 82 of the second 3D scout ultrasound scan from the second position P2. The triangular view cone 83 in FIG. 5 indicates the position and orientation of the first 2D ultrasound image with respect to the first and second 3D scout ultrasound images.

Referring again to FIG. 3, the first 3D scout ultrasound image 3 and the first 2D ultrasound image 4 of the volumetric region can be obtained from a memory unit or database 60. In an advantageous embodiment, the memory unit can be a database such as PACS (picture archiving and communication system) of a hospital, a cloud-based database or a local storage unit within an ultrasound device. Such a database 60 can also be provided in the systems as shown in FIG. 1 and FIG. 2. The respective first 2D ultrasound image and first 3D scout ultrasound image are stored together with data indicative of their relative position and/or orientation with respect to each other. The first 3D scout ultrasound image and the first 2D ultrasound image can be images acquired with a 3D ultrasound probe from a first position. The position and orientation of the first 2D ultrasound image with respect to the first 3D scout ultrasound image can be determined for example from control parameters of the ultrasound probe for acquisition of the first 2D ultrasound image and the first 3D scout ultrasound image. Control parameters may comprise one or more of an acquisition gain, focus, depth, zoom, position, orientation and/or beam steering parameter.

The system 100 further comprises an ultrasound probe 14 comprising an ultrasound transducer array 26 arranged to acquire an ultrasound image of a subject 12. The ultrasound probe 14 can be an ultrasound probe as for example described with reference to FIG. 1 and FIG. 2. The ultrasound probe 14 provides the second 3D scout ultrasound image 6 as a further input to the medical ultrasound image processing device 10.

The medical ultrasound image processing device 10 comprises a first interface 2 for receiving a first 3D scout ultrasound image 3 and a first 2D ultrasound image 4 of a volumetric region of the subject 12; a second interface 5 for receiving a second 3D scout ultrasound image 6 of the volumetric region; and a processing unit 11 arranged to perform the steps of determining an orientation of an image plane of the first 2D ultrasound image 4 with respect to the first 3D scout ultrasound image 3; registration of the first 3D scout ultrasound image 3 and the second 3D scout ultrasound image 6 in a common coordinate frame; determining an orientation of the image plane of the first 2D ultrasound image 3 with respect to said common coordinate frame based on said registration of the first and second 3D scout ultrasound images 4, 6 and the determined orientation of the image plane of the first 2D ultrasound image 4 with respect to the first 3D scout ultrasound image 3; and providing a control signal 8 adapted to control an acquisition of a second 2D ultrasound image of the volumetric region by an ultrasound probe 14 in accordance with the orientation of the image plane of the first 2D ultrasound image 4 of the volumetric region, wherein an orientation of an image plane of the second 2D ultrasound image corresponds to the determined orientation of the image plane of the first 2D ultrasound image 4 of the volumetric region. The control signal 8 can be provided via an output 7 of the image processing device 10.

The system can optionally further comprise a probe controller 31 arranged to control the ultrasound probe 14 to acquire the second 2D ultrasound image based on the control signal 8 provided by said medical ultrasound image processing device 10. Alternatively, the control signal 8 can be adapted to directly control the ultrasound probe 14.

Advantageously, the second 3D scout ultrasound image is an image acquired with a 3D ultrasound probe 14 from a second position. Since the measurement is fast, such as for example $1/10^{th}$ of a second, it can be assumed that the ultrasound probe 14 is not repositioned between acquisition of the second 3D scout ultrasound image and the second 2D ultrasound image. The control signal 8 can thus be provided for the acquisition of the second 2D ultrasound image under the assumption or boundary condition that the second 2D ultrasound image is acquired from the same second position. The control signal can be indicative of a control parameter of the ultrasound probe, such as a beam steering parameter, to be used for acquisition of the second 2D ultrasound image. Thereby, an orientation of an image plane for acquisition of the second 2D ultrasound image can be set electronically or electronically steered and brought into correspondence with the determined orientation of the image plane of the first 2D ultrasound image. Referring again to FIG. 5, the first and the second 2D ultrasound image then consistently provide the same view 84 as indicated by the triangular view cone 83 of the first 2D image ultrasound.

Referring again to FIGS. 1 and 2, the proposed medical ultrasound image processing device can be included in the image reconstruction unit 16, in particular in the image processor 42. The image processor 42 may thus be connected to a database 60 for receiving the first 3D scout ultrasound image and the first 2D ultrasound image. As shown in FIG. 2, probe controller 31 can be implemented by the transducer controller 32 which is connected to the image processor 42.

Figure 4:
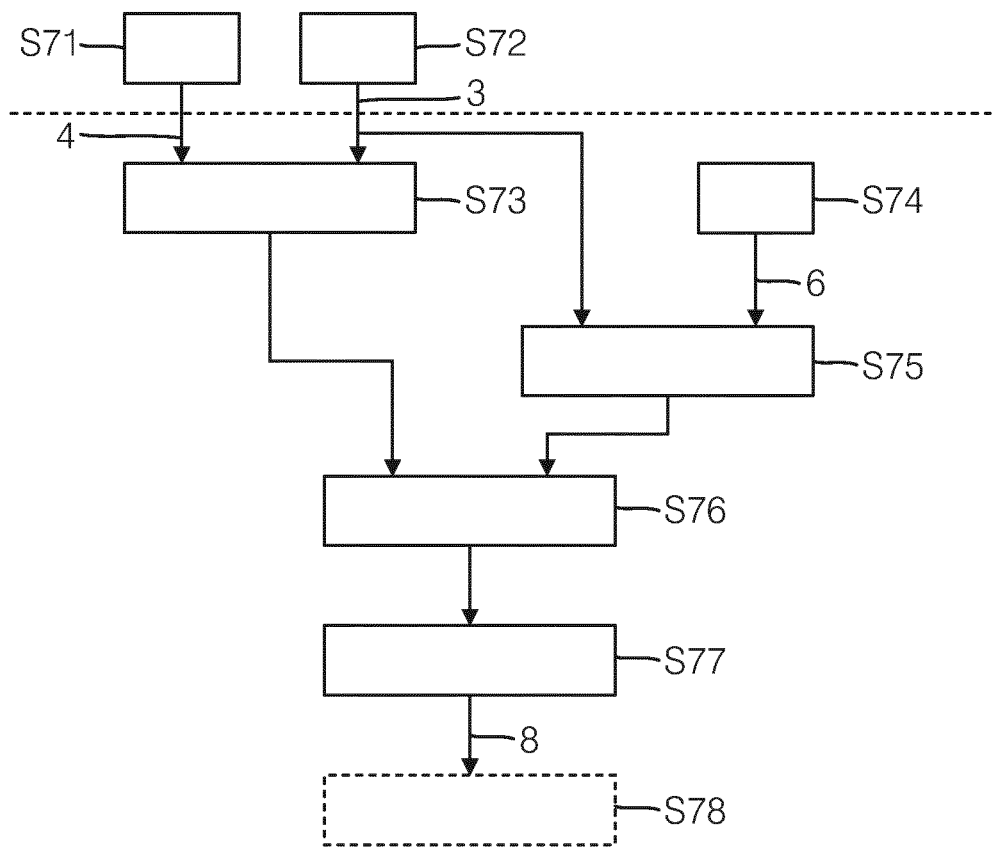
FIG. 4 shows a flow chart of a first embodiment of a medical image processing method according to an aspect of the present invention.

FIG. 4 shows a flow chart a workflow comprising the medical image processing method according to an aspect of the present invention. Elements above the horizontal dashed line refer to an initial examination, elements below the horizontal dashed line refer to a follow-up examination.

In a first step S71, a first 2D ultrasound image is acquired. In a second step S72, a first 3D scout ultrasound image is acquired. The sequence may be changed. The first 3D scout ultrasound image and the first 2D ultrasound image are advantageously acquired together, i.e. images acquired during the same examination, advantageously without repositioning the ultrasound probe. The first 2D ultrasound image and the first 3D scout ultrasound image are stored together with data indicative of their relative position and/or orientation with respect to each other.

In step S73, an orientation and/or position of the first 2D ultrasound image is determined with respect to the first 3D scout ultrasound image. This step can also already be performed before the follow-up examination. The medical ultrasound image processing unit 10 may thus receive the first 3D scout ultrasound image, the first 2D ultrasound image and data indicative of their relative position and/or orientation with respect to each other. In step S74, a second 3D scout ultrasound image is acquired. As exemplarily shown in FIG. 1, due to the handheld acquisition of ultrasound images, wherein the ultrasound probe 14 is manually positioned by the physician, a position P1 of the ultrasound probe 14 during the initial examination will normally differ from a position P2 of the ultrasound probe 14' during the follow-up examination. This is also illustrated by the different 3D view cones 81 and 82 in FIG. 5.

In step S75, the first 3D scout ultrasound image 3 and the second 3D scout ultrasound image 6 are registered in a common coordinate frame. In other words, a relative position and/or orientation of the first 3D scout ultrasound image and the second 3D scout ultrasound image is determined. Hence, a correspondence between the first 3D scout ultrasound image and the second 3D scout ultrasound image can be established. Known image registration techniques can be employed. The step of registration can optionally further comprise the step of determining whether there is a sufficient overlap of said 3D ultrasound images. If not, a control signal for iterative acquisition of second 3D scout ultrasound images can be provided by the image processing device. Optionally, if the 3D scouts do not overlap enough, the sonographer can be prompted to change the position of the probe and to acquire a new second 3D scout ultrasound image. A sequence of second 3D ultrasound images can be acquired iteratively, advantageously until a sufficient overlap for reliable registration of the 3D ultrasound images or for acquisition of the second 2D ultrasound image has been reached.

In step S76, an orientation of the image plane of the first 2D ultrasound image with respect to said common coordinate frame is determined based on said registration (see step S75) of the first and second 3D scout ultrasound images and the determined orientation (see step S73) of the image plane of the first 2D ultrasound image with respect to the first 3D scout ultrasound image.

In step S77, a control signal 8 adapted to control an acquisition of a second 2D ultrasound image of the volumetric region by an ultrasound probe in accordance with the orientation of the image plane of the first 2D ultrasound image of the volumetric region is provided, wherein an orientation of an image plane of the second 2D ultrasound image corresponds to the determined orientation of the image plane of the first 2D ultrasound image of the volumetric region. Thereby, the image processing device 10 can control the ultrasound probe 14 to acquire a second 2D ultrasound image with the same view as the first 2D ultrasound image. Hence, even though the 3D view cones 81, 82 of the first 3D scout ultrasound image in an initial examination and the second 3D scout ultrasound image in a follow-up examination differ from each other, both 2D ultrasound images can provide the same view as indicated by the view cones 83 and 84 as shown in FIG. 5.

Advantageously, the second 2D ultrasound image is acquired steps during the same follow-up examination immediately after the second 3D scout ultrasound image and the aforementioned processing, without repositioning the ultrasound probe. Thereby, no tracking of a position of the ultrasound probe between measurements is required.

It shall be understood that the data acquisition steps S71, S72, S74 and S78 can precede or follow, respectively, the actual signal processing which can then be performed without sensing means based on such data by a processing device such as a microprocessor or microcontroller, wherein program code means cause the processor to carry out the processing steps described herein.

Figure 6:
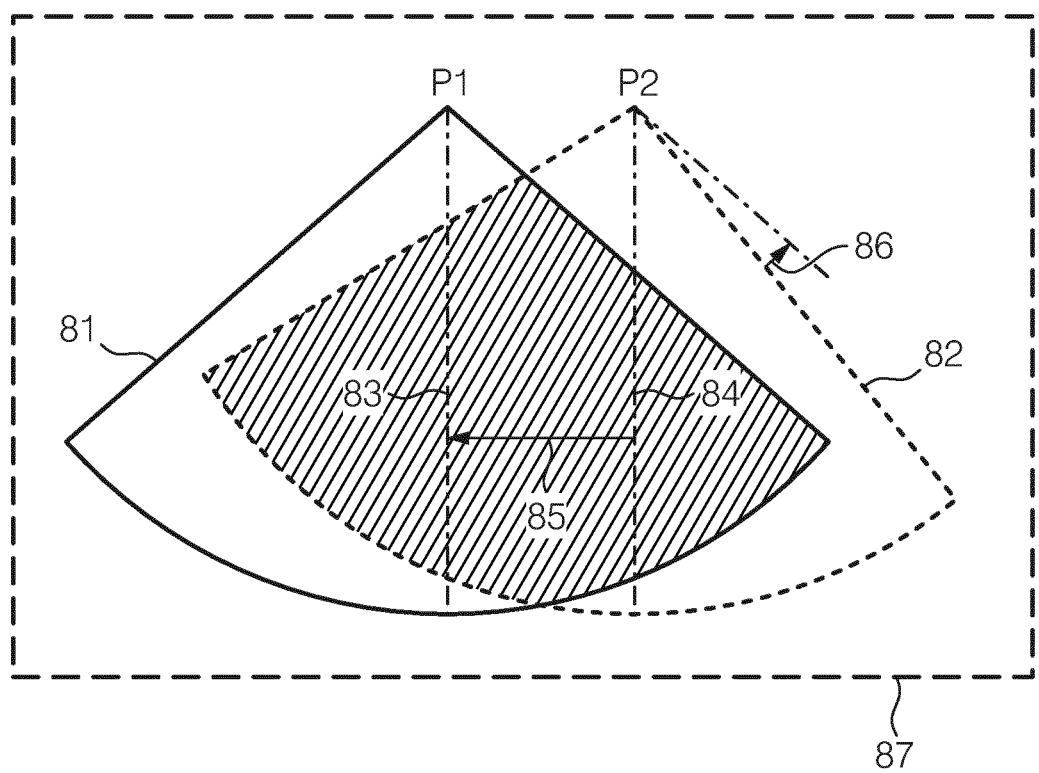
FIG. 6 shows a second schematic illustration of an orientation of respective 2D and 3D ultrasound images with respect to each other.

FIG. 6 shows a second schematic illustration of a position and orientation of respective 2D and 3D ultrasound images with respect to each other. For simplicity, FIG. 6 shows a two-dimensional cross-section perpendicular to the image planes of the 2D ultrasound images 83, 84. A first view cone 81 of the first 3D scout ultrasound image is acquired from a first position P1. A second view 82 cone of the second 3D scout ultrasound image is acquired from a second position P2. A view cone or image plane of the first 2D ultrasound image is denoted by reference numeral 83. A view cone or image plane of the second 2D ultrasound image is denoted by reference numeral 84.

The first 3D scout image is registered (S75) with respect to the second 3D scout ultrasound image to determine a relative position and orientation. The registration can comprise determining an overlap between the first 3D scout ultrasound image and the second 3D scout ultrasound image, as indicated by the shaded region in FIG. 6. Furthermore, the processing unit is arranged to determine an orientation of the image plane 83 of the first 2D ultrasound image with respect to the first 3D scout ultrasound image (S73).

Based on the known orientation of the image plane 83 of the first 2D ultrasound image with respect to view cone 81 of the first 3D scout ultrasound image, and further based the known relative position and orientation of the first 3D scout ultrasound image as indicated by view cone 81 with respect to the second 3D scout ultrasound image as indicated by view cone 82, an orientation of the image plane 84 for acquisition of the second 2D ultrasound image with respect to the second 3D scout ultrasound image can be calculated, such that the orientation of said second 2D ultrasound image corresponds to the orientation of the first 2D ultrasound image. Hence, a control signal can be provided by the proposed image processing device 10 to control an acquisition of a second 2D ultrasound image of the volumetric region by an ultrasound probe in accordance with the orientation of the image plane of the first 2D ultrasound image of the volumetric region, wherein an orientation of an image plane 84 of the second 2D ultrasound image corresponds to the determined orientation of the image plane 83 of the first 2D ultrasound image of the volumetric region.

Advantageously, the image processing device is arranged to provide guidance to the sonographer for acquisition of the second 2D ultrasound image based on said control signal via a user interface such as the display 18 of the ultrasound system 100 of FIG. 1 and FIG. 2. For example, a view as shown in frame 87 in FIG. 6 can be displayed on a graphical user interface (GUI) as a help or guidance to the sonographer to move the ultrasound probe 14' in a way that the ultrasound probe position P2 of the follow-up examination corresponds better to the ultrasound probe position P1 of the initial examination. The sonographer can thus be provided with guidance such as moving the ultrasound probe as indicated by arrow 85 and optionally further tilting the ultrasound probe by an angle as indicated by 86. If the image planes 83, 84 of the respective 2D ultrasound images have the same position and orientation with respect to the view cones 81, 82 of the 3D scout ultrasound images, the first and second 2D ultrasound images can be acquired with identical views.

Alternatively or in addition, the sonographer can be provided with voice guidance on how to position the ultrasound probe for acquisition of the second 2D ultrasound image. For this purpose, the ultrasound system can feature a user interface comprising an audio output unit such as a speaker.

In an embodiment, electronic beam steering can be applied to adjust an angle of the image plane 84. An advantage of this embodiment is that it is not required to tilt the ultrasound probe manually as indicated by 86. This can be the case when having a 3D ultrasound system with a matrix transducer. Hence, providing guidance to the sonographer and adjusting parameters of the ultrasound probe can be advantageously combined for acquisition of the second 2D ultrasound image based on the control signal.

The image processing device can also be arranged to provide a control signal for acquisition of the second 2D ultrasound image by controlling parameters of the ultrasound probe only. Hence, for the exemplary case shown in FIG. 6, the ultrasound probe can be controlled to acquire the second 2D ultrasound image as the intersection of the image plane 83 of the first 2D ultrasound image with the view cone 82 of the second 3D scout ultrasound image. An advantage is that the ultrasound probe does not have to be repositioned. However, a disadvantage can be that only a subsection of the complete view of the initial 2D image can be acquired.

In a further embodiment, for example, wherein a 2D image plane 83, 84, needs to pass through the probe position P1, P2 and the 2D image plane cannot be arbitrarily shifted without moving the ultrasound probe, the image plane 84 of the second 2D ultrasound image can also be controlled to approximately correspond to the image plane 83 of the first 2D image. For example, an orientation of the image plane 84 of the second 2D ultrasound image corresponds to the determined orientation of the image plane 83 of the first 2D ultrasound image of the volumetric region. Hence, a parallel image plane 84 or a plane with minimum overall distance (in the common field-of-view) can be provided with respect to the image plane 83 of the first 2D ultrasound image. Nonetheless, in a preferred embodiment the position and the orientation of the 3D and 2D ultrasound images are determined and considered.

It is to be understood, that even though FIG. 6 shows a simplified two-dimensional view, also a rotation may have to be considered to bring the 2D image planes of the first and second 2D ultrasound images into correspondence in 3D space.

Figure 7:
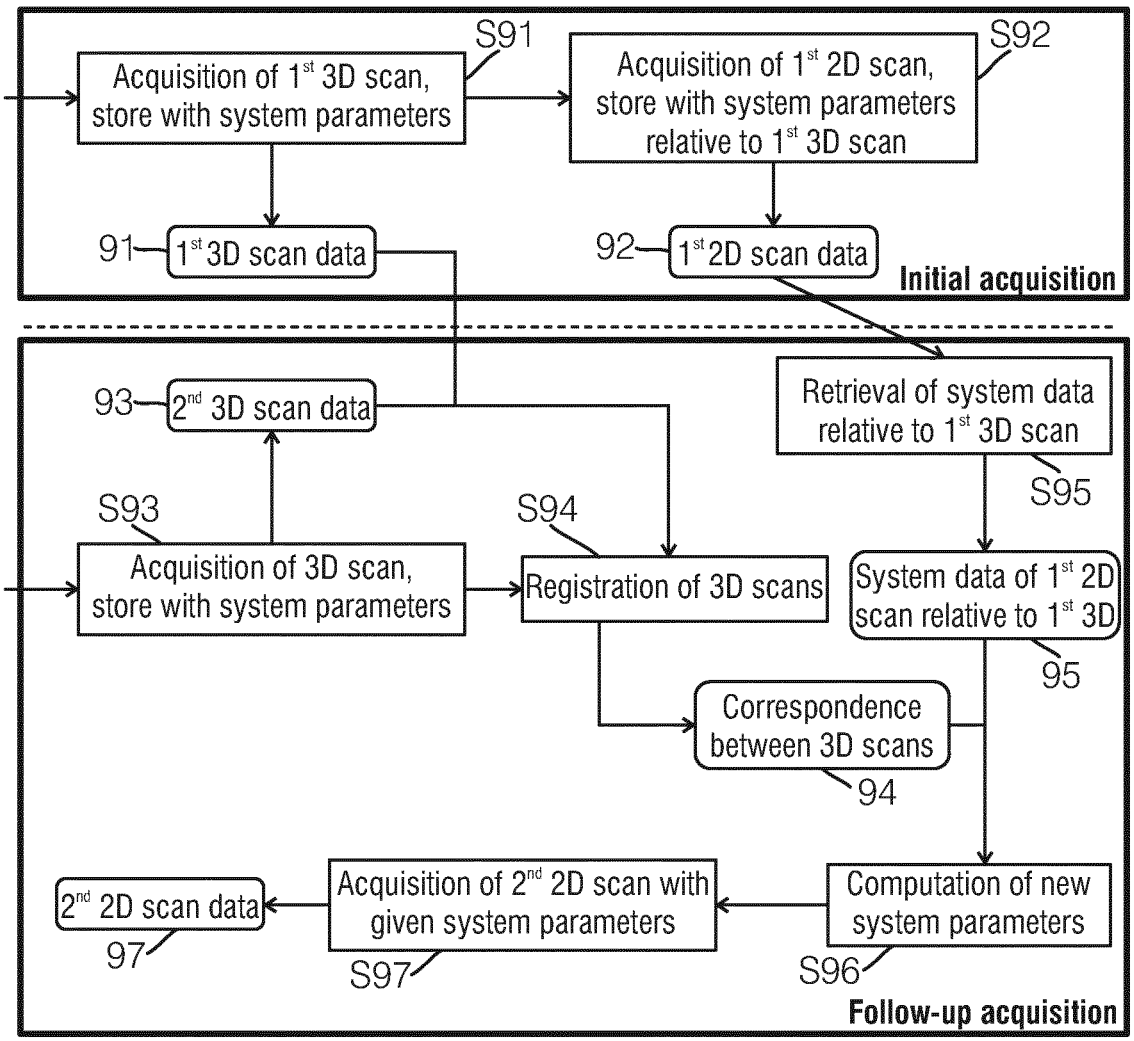
FIG. 7 shows a flow chart of a proposed workflow for supporting reproducible acquisition of 2D ultrasound images.

FIG. 7 shows a second flow chart of a proposed workflow for supporting reproducible acquisition of 2D ultrasound images. Elements above the horizontal dashed line again refer to an initial acquisition, elements below the horizontal dashed line refer to a follow-up acquisition.

In step S91, a first 3D scout ultrasound scan is acquired and stored with system parameters of the ultrasound system used for acquisition such as acquisition gain, focus, depth, zoom, position, orientation and beam steering parameters. The corresponding stored first 3D ultrasound scan data is denoted by item 91. In step S92, a first 2D scan is acquired and stored with the corresponding system parameters of the ultrasound system. The corresponding stored first 2D ultrasound scan data is denoted by item 92.

In step S93, a second 3D scout ultrasound scan is acquired and stored with system parameters of the ultrasound system used for acquisition. The corresponding stored second 3D scan data is denoted by item 93. In step S94, a registration of the first 3D scout ultrasound scan and the second 3D scan is carried out based on the stored first 3D scan data 91 and the stored second 3D scan data 93. The output 94 of this step is a correspondence between said 3D scout ultrasound scans and thus gives a relative position and/or orientation of the first and second 3D scout ultrasound scans with respect to each other. In step S95, system data or system parameters of the first 2D ultrasound scan relative to the first 3D scout ultrasound scan are retrieved based on the stored first 3D scan data 91 and the stored first 2D scan data 92. The output 95 of this step is system data or system parameters of the first 2D ultrasound scan relative to the first 3D scout ultrasound scan and can thus give a relative position and/or orientation of the first 2D scan and the first 3D scans with respect to each other.

In step S96, system parameters for acquisition of the second 2D ultrasound scan are computed based on the correspondence between the 3D scout ultrasound scans and the system data or system parameters of the first 2D ultrasound scan relative to the first 3D scout ultrasound scan. A control signal indicative of these system parameters can be provided to the ultrasound probe 14. In step S97, the second 2D ultrasound scan is acquired based on said system parameters for acquisition of the second 2D ultrasound scan. A 2D plane can advantageously be set electronically, i.e., via electronic beam steering, when having a 3D system with a matrix transducer. The corresponding second 2D scan data is denoted by reference numeral 97.

Given a first 2D ultrasound scan with corresponding first 3D scout ultrasound scan and known system parameters indicative of their relative position and/or orientation, a 2D ultrasound scan with an identical view thus can be acquired. To this end, a follow-up, second 3D scout ultrasound scan has to be acquired and registered with the initial, first 3D scout ultrasound scan. Knowing the correspondence between the 3D scout ultrasound scan and the system parameters of the initial, first 2D ultrasound scan relative to the first 3D scout ultrasound scan, the system parameters for the follow-up 2D ultrasound scan can thus be deduced.

In a practical application, a physician may thus provide a first 2D ultrasound image together with a corresponding 3D scout ultrasound image of known relative position and/or orientation as inputs and then request the acquisition of a new 2D ultrasound image with a view corresponding to said first 2D ultrasound image. The proposed image processing unit may then automatically trigger the acquisition of a second 3D scout ultrasound image, perform the image processing method described herein, and provide the physician with the desired second 2D image.

In a further embodiment, an atlas containing information on standard views or measurements can be used to acquire consistent images. In this case, the first 2D ultrasound image and the first 3D scout ultrasound image can be reference images from the atlas, i.e., not previous images from the subject currently being examined. The atlas can then be matched to the second 3D scout ultrasound image and then the correct slice and orientation for the second 2D ultrasound image can be deduced with the method proposed herein. This can be particularly useful, for example, in fetal ultrasound to reproducibly measure the diameter of the head.

In conclusion, the solutions proposed herein thus provide a device and method which support more consistent and/or reliable acquisition of 2D ultrasound images.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical ultrasound image processing device, comprising:
    a first interface adapted to receive a first 3D scout ultrasound image and a first 2D ultrasound image of a volumetric region;
    a second interface adaptive to receive a second 3D scout ultrasound image of the volumetric region;
    a processor;
    a non-transitory computer-readable recording medium that stores instructions, which when executed by the processor, cause the processor to:
        determine an orientation of an image plane of the first 2D ultrasound image with respect to the first 3D scout ultrasound image;
        register the first 3D scout ultrasound image and the second 3D scout ultrasound image in a common coordinate frame;
        determine an orientation of the image plane of the first 2D ultrasound image with respect to the common coordinate frame based on the registration of the first and second 3D scout ultrasound images and the determined orientation of the image plane of the first 2D ultrasound image with respect to the first 3D scout ultrasound image; and
        provide a control signal adapted to provide one or more control parameters for acquisition of a second 2D ultrasound image of the volumetric region by an ultrasound probe in accordance with the orientation of the image plane of the first 2D ultrasound image of the volumetric region,
    wherein an orientation of an image plane of the second 2D ultrasound image corresponds to the determined orientation of the image plane of the first 2D ultrasound image of the volumetric region,
    wherein the acquisition of the second 2D ultrasound image by the ultrasound probe is from either a same position as, or a tracked position with respect to, a position of the acquisition of the second 3D scout ultrasound image.

2. The medical ultrasound image processing device as claimed in claim 1,
    wherein the first 3D scout ultrasound image and the first 2D ultrasound image are images acquired with a first 3D ultrasound probe from a first position; and
    wherein the second 3D scout ultrasound image is an image acquired with a second 3D ultrasound probe from a second position.

3. The medical ultrasound image processing device as claimed in claim 1, wherein the instructions further cause the processor to determine the orientation of the image plane of the first 2D ultrasound image with respect to the first 3D scout ultrasound image based on control parameters of the ultrasound probe for acquisition of the first 2D ultrasound image and the first 3D scout ultrasound image.

4. The medical ultrasound image processing device as claimed in claim 1, wherein at least one of the ultrasound images further comprises metadata indicative of a control parameter of an ultrasound probe for acquisition of the ultrasound images.

5. The medical ultrasound image processing device as claimed in claim 1, wherein the control signal is indicative of at least one control parameter of the ultrasound probe for acquisition of the second 2D ultrasound image.

6. The medical ultrasound image processing device as claimed in claim 1, wherein the step of registration comprises an anatomy segmentation the first and second 3D scout ultrasound images.

7. The medical ultrasound image processing device as claimed in claim 1, wherein the registration of the second 3D scout ultrasound image with the first 3D scout ultrasound image comprises a registration of an image content within field-of-view masks of the first 3D scout ultrasound image and the second 3D scout ultrasound image respectively.

8. The medical ultrasound image processing device as claimed in claim 1, wherein the registration comprises determining an overlap between the first 3D scout ultrasound image and the second 3D scout ultrasound image, in particular determining whether there is a sufficient overlap of the 3D scout ultrasound images.

9. The medical ultrasound image processing device as claimed in claim 1, wherein a resolution of the first and/or second 2D ultrasound image is higher than a resolution of the first and/or second 3D scout ultrasound image.

10. The medical ultrasound image processing device as claimed in claim 1, wherein instructions further cause the processor to determine a position of the first 2D ultrasound image with respect to the first 3D scout ultrasound image and/or the common coordinate frame and further arranged to provide a control signal adapted to control an acquisition of the second 2D ultrasound image by an ultrasound probe in accordance with the position of the first 2D ultrasound image of the volumetric region.

11. The medical ultrasound image processing device as claimed in claim 1, further arranged to provide guidance to a sonographer for acquisition of the second 2D ultrasound image based on the control signal via a user interface, in particular arranged to provide voice guidance or graphical guidance on how to position the ultrasound probe for acquisition of the second 2D ultrasound image.

12. An ultrasound system for imaging a volumetric region comprising:
    an ultrasound probe comprising an ultrasound transducer array arranged to acquire an ultrasound image of a subject;
    the medical ultrasound image processing device as claimed in claim 1; and
    a probe controller arranged to control the ultrasound probe to acquire the second 2D ultrasound image based on the control signal provided by the medical ultrasound image processing device from either a same position as, or at a tracked position with respect to, the position of the acquisition of the second 3D scout ultrasound image.

13. A medical imaging method, comprising
obtaining a first 3D scout ultrasound image and a first 2D ultrasound image of a volumetric region;
obtaining a second 3D scout ultrasound image of the volumetric region;
determining an orientation of an image plane of the first 2D ultrasound image with respect to the first 3D scout ultrasound image;
registration of the first 3D scout ultrasound image and the second 3D scout ultrasound image in a common coordinate frame;
determining an orientation of the image plane of the first 2D ultrasound image with respect to the common coordinate frame based on the registration of the first and second 3D scout ultrasound images and the determined orientation of the image plane of the first 2D ultrasound image with respect to the first 3D scout ultrasound image; and
providing a control signal adapted to provide one or more control parameters for acquisition of a second 2D ultrasound image of the volumetric region by an ultrasound probe in accordance with the orientation of the image plane of the first 2D ultrasound image of the volumetric region, wherein an orientation of an image plane (84) of the second 2D ultrasound image corresponds to the determined orientation of the image plane of the first 2D ultrasound image of the volumetric region,
wherein the acquisition of the second 2D ultrasound image by the ultrasound probe is from either a same position as, or a tracked position with respect to, a position of the acquisition of the second 3D scout ultrasound image.

14. The method as claimed in claim 13 further comprising the step of acquisition of the second 2D ultrasound image of the volumetric region with the ultrasound probe based on the control signal.

15. A tangible, non-transitory computer readable medium, which stores instructions, which when executed by a processor, causes the processor to:
determine an orientation of an image plane of a first 2D ultrasound image with respect to a first 3D scout ultrasound image;
register the first 3D scout ultrasound image and a second 3D scout ultrasound image in a common coordinate frame;
determine an orientation of the image plane of the first 2D ultrasound image with respect to the common coordinate frame based on the registration of the first and second 3D scout ultrasound images and the determined orientation of the image plane of the first 2D ultrasound image with respect to the first 3D scout ultrasound image; and
provide a control signal adapted to provide one or more control parameters for acquisition of a second 2D ultrasound image of a volumetric region by an ultrasound probe in accordance with the orientation of the image plane of the first 2D ultrasound image of the volumetric region.

16. The tangible, non-transitory computer readable medium as claimed in claim 15, wherein at least one of the ultrasound images further comprises metadata indicative of a control parameter of an ultrasound probe for acquisition of the ultrasound images.

17. The tangible, non-transitory computer readable medium as claimed in claim 15, wherein the one or more control parameters comprises at least one of gain parameter, a focus parameter, a depth parameter, a zoom parameter, a position parameter, an orientation and a beam steering parameter.

18. Tangible, non-transitory computer readable medium as claimed in claim 15, wherein the one or more control parameters comprise a relative position and/or orientation parameter of a desired second 2D ultrasound image to be acquired with respect to the second 3D scout ultrasound image.

19. The medical ultrasound image processing device as claimed in claim 1, wherein the one or more control parameters comprise one or more of an acquisition gain parameter, a focus parameter, a depth parameter, a zoom parameter, a position parameter, an orientation and a beam steering parameter.

20. The medical ultrasound image processing device as claimed in claim 1, wherein the one or more control parameters comprise a relative position and/or orientation parameter of a desired second 2D ultrasound image to be acquired with respect to the second 3D scout ultrasound image.

21. The method as claimed in claim 13, wherein the one or more control parameters comprise one or more of an acquisition gain parameter, a focus parameter, a depth parameter, a zoom parameter, a position parameter, an orientation and a beam steering parameter.

22. The method as claimed in claim 13, wherein the one or more control parameters comprise a relative position and/or orientation parameter of a desired second 2D ultrasound image to be acquired with respect to the second 3D scout ultrasound image.

* * * * *